US009610393B2

(12) United States Patent
Rada et al.

(10) Patent No.: US 9,610,393 B2
(45) Date of Patent: Apr. 4, 2017

(54) APPARATUS AND METHOD FOR THE TREATMENT OF BLOOD WITH SELECTIVE EXTRACTION OF SOLUTES

(75) Inventors: Hiram Rada, Lyons (FR); Nicolas Semenzato, Décines Charpieu (FR)

(73) Assignee: Gambro Lundia AB, Lund (SE)

( * ) Notice: Subject to any disclaimer, the term of this patent is extended or adjusted under 35 U.S.C. 154(b) by 249 days.

(21) Appl. No.: 13/292,804

(22) Filed: Nov. 9, 2011

(65) Prior Publication Data

US 2012/0118801 A1 May 17, 2012

(30) Foreign Application Priority Data

Nov. 10, 2010 (EP) ...................................... 10014442

(51) Int. Cl.
| | | |
|---|---|---|
| *B01D 61/24* | (2006.01) | |
| *B01D 61/32* | (2006.01) | |
| *A61M 1/34* | (2006.01) | |
| *A61M 1/14* | (2006.01) | |
| *B01D 61/22* | (2006.01) | |
| *B01D 61/28* | (2006.01) | |
| *C02F 1/44* | (2006.01) | |

(52) U.S. Cl.
CPC .......... *A61M 1/342* (2013.01); *A61M 1/3434* (2014.02); *A61M 1/3472* (2013.01); *B01D 61/243* (2013.01); *B01D 61/22* (2013.01); *B01D 61/28* (2013.01); *B01D 2311/06* (2013.01); *B01D 2311/14* (2013.01); *C02F 1/44* (2013.01); *C02F 1/444* (2013.01)

(58) Field of Classification Search
CPC ...... A61M 1/34; A61M 1/342; A61M 1/3413; A61M 1/3472; A61M 1/3621; A61M 1/3639; A61M 1/3663; A61M 2001/3434; A61M 2001/34; A61M 2001/341; A61M 2001/3413; A61M 2001/3417; A61M 2001/3482; A61M 2001/3601; A61M 2001/3621; A61M 1/3434; A61M 1/3448; A61M 1/3641
USPC ....... 210/739, 741, 85, 87, 90, 97, 103, 137; 604/4.01, 5.01, 30, 31, 505, 65, 67
See application file for complete search history.

(56) References Cited

U.S. PATENT DOCUMENTS

| | | | | |
|---|---|---|---|---|
| 4,350,594 | A * | 9/1982 | Kawai et al. .................. | 210/637 |
| 4,708,802 | A * | 11/1987 | Rath et al. ..................... | 210/641 |
| 4,715,786 | A * | 12/1987 | Wolff et al. ...................... | 417/22 |
| 4,936,980 | A * | 6/1990 | Harada ............... | A61M 1/3496 |
| | | | | 210/321.65 |
| 5,476,592 | A * | 12/1995 | Simard ......................... | 210/651 |
| 5,702,594 | A * | 12/1997 | Yamasaki et al. ............ | 210/151 |
| 6,039,877 | A * | 3/2000 | Chevallet et al. ............ | 210/636 |
| 6,193,681 | B1 | 2/2001 | Davidner | |

(Continued)

FOREIGN PATENT DOCUMENTS

| | | |
|---|---|---|
| EP | 0 615 780 A1 | 9/1994 |
| EP | 0 615 780 B1 | 4/2001 |

*Primary Examiner* — David C Mellon
*Assistant Examiner* — Pranav Patel
(74) *Attorney, Agent, or Firm* — Mueting, Raasch & Gebhardt, P.A.

(57) ABSTRACT

Extracorporeal blood treatment apparatus and methods including a main treatment unit and an auxiliary treatment unit, along with one or more sensors for determining a parameter related to a pressure drop across the auxiliary treatment unit, and a control unit configured to control a flow regulator at least based on the parameter value.

18 Claims, 5 Drawing Sheets

(56) References Cited

U.S. PATENT DOCUMENTS

| | | | |
|---|---|---|---|
| 6,406,631 B1* | 6/2002 | Collins et al. | 210/646 |
| 6,716,356 B2* | 4/2004 | Collins et al. | 210/646 |
| 7,758,532 B2* | 7/2010 | Mori et al. | 604/5.01 |
| 2003/0017146 A1 | 1/2003 | Tepic | |
| 2004/0060866 A1* | 4/2004 | Radunsky et al. | 210/647 |
| 2004/0167457 A1* | 8/2004 | Tonelli et al. | 604/6.09 |
| 2004/0182787 A1 | 9/2004 | Chevallet | |
| 2007/0062861 A1* | 3/2007 | Lannoy | 210/501 |
| 2008/0215247 A1* | 9/2008 | Tonelli et al. | 702/19 |
| 2008/0243045 A1* | 10/2008 | Pasqualini | 604/5.04 |
| 2009/0084717 A1* | 4/2009 | Delmage et al. | 210/108 |
| 2009/0151470 A1* | 6/2009 | Puppini et al. | 73/861 |

\* cited by examiner

APPARATUS AND METHOD FOR THE TREATMENT OF BLOOD WITH SELECTIVE EXTRACTION OF SOLUTES

Apparatus and methods for the treatment of blood with selective extraction of solutes. The description relates in particular to filtration of blood using two or more treatment units to selectively separate and extract substances of selected molecular size.

BACKGROUND

Blood contains solutes with different molecular weights: for example, urea has molecular weight 60 Daltons, phosphate has molecular weight 96-97 Daltons, creatinine has molecular weight 113 Daltons, vitamin B12 has molecular weight 1355 Daltons, insulin has molecular weight 5200 Daltons, beta 2-microglobulin has molecular weight 12000 Daltons, and albumin 68000 Daltons.

In the field of dialysis, the first membranes used were highly permeable to small solutes of molecular weight up to 200 Daltons. The clearance of small solutes depends on the permeability and diffusion capacity of the membrane used. The lack of permeability of these membranes for certain medium-sized solutes in the vitamin B12 range (1355 Daltons) was considered as one of the causes determining the occurrence of multiple uremic neuropathies.

To improve the clearance of medium-sized molecules, a first response was to add to the diffusion flow through the membrane a convection flow using high flow membranes with a molecular size cut-off value of 40,000 Daltons. These membranes caused, however, loss of useful plasma constituents such as hormones, vitamins and amino acids.

A further solution for improving clearance of medium-sized molecules is hemofiltration, a purely convective method for the elimination of solutes by the membrane. However, this method extracts a large amount of liquid from blood thereby requiring reinjection of sterile liquid into the blood, and a membrane that is highly permeable to solutes of molecular weight up to 40,000 Daltons. However, in a purely convective mode, the clearance of small-sized molecules is poor.

A further method where hemofiltration and hemodialysis were combined is known as haemo-diafiltration. However, problems that arise include difficulty in precisely controlling the haemo-filtration flow, high loss of hormones and amino acids, the complexity of the system, the large quantities of sterile liquid and dialysate necessary, and consequently the high cost of the treatment. In order to offer a better solution capable of clearance of more selective clearance of blood solutions have been conceived using two or more filtration units.

For instance, U.S. Pat. No. 6,193,681 describes an apparatus to treat septicaemia in the blood. The blood flows first through a UV irradiation device and then through a blood concentrator before re-injection in the patient. A secondary circuit is connected to a second outlet from the blood concentrator from which the fluid flows out through a filter followed by a membrane module and a dilution source, and is then injected upstream of the blood concentrator.

Furthermore, US2004182787 discloses a system combining two or more filtration units where the fluid ultrafiltered through a first treatment unit is treated by a second unit before being re-injected in the extracorporeal blood circuit. This solution offered good clearance, while consuming small amounts of sterile liquid.

As used herein, the expression "cut-off" refers to the Molecular Weight Cut Off (MWCO) which is measured in Dalton. The MWCO is defined as the minimal molecular weight of a globular molecule which is retained by the membrane to at least about 90%.

As used herein the expression "small-sized molecules" refers to molecules of molecular weight less than about 2000 Daltons.

As used herein, the expression "medium-sized molecules" refers to molecules of molecular weight between about 2000 Daltons and about 50,000 Daltons. Among medium sized molecules the following subgroups can be identified: "small middle molecules" refers to molecules with size in the range from about 5000 Daltons to about 30,000 Daltons and "large middle molecules" refers to molecules with size in the range from 30,000 Daltons to 50,000 Daltons.

As used herein, "large-sized molecules" refers to molecules of molecular weight greater than about 50,000 Daltons (for example, proteins).

SUMMARY

Apparatus and methods for the treatment of blood with selective extraction of solutes are described herein. In some embodiments, the apparatus and methods may involve filtration of blood using two or more treatment units to selectively separate and extract substances of selected molecular size.

In some embodiments, the control of the rates of fluids through certain lines of the system in order to have a controlled efficiency throughout a treatment time may offer advantages in processing.

In some embodiments, it may be advantageous to offer apparatus and methods as described herein using multiple filtration units which is suitable for the selective extraction of solutes having molecules falling in a defined range and which may, in addition, be capable of maintaining a substantially constant ability to extract said solutes during the treatment.

Apparatus and processes for the extracorporeal treatment of blood according to some potential aspects of the invention are described below.

A first aspect relates to an extracorporeal blood treatment apparatus comprising:
  at least a main treatment unit comprising a first compartment and a second compartment separated by a semipermeable membrane,
  a blood withdrawal line for blood to be treated connected to an inlet of the first compartment of the main treatment unit,
  a blood return line connected to an outlet of the first compartment of the main treatment unit, wherein the blood return line, the blood withdrawal line and the first compartment are part of an extracorporeal blood circuit,
  at least an auxiliary treatment unit comprising at least one fluid inlet and at least one fluid outlet,
  a first fluid line having a first end connected to an outlet of the second compartment of the main treatment unit and a second end connected to the fluid inlet of the auxiliary treatment unit,
  a second fluid line having a first end connected to the fluid outlet of the auxiliary treatment unit and a second end connected to said extracorporeal blood circuit,
  a fluid flow regulator for regulating the flow of fluid through the semipermeable membrane of the main treatment unit, at least one sensor for determining a parameter related to a pressure drop across said auxiliary treatment unit and emitting a corresponding pressure signal, and a control unit configured to execute a control procedure comprising:

receiving said pressure signal from the sensing means and determining a corresponding parameter value, and controlling the flow regulator at least based on said parameter value.

In a second aspect according to the first aspect the fluid flow regulator comprises one selected in the group including:

one or more pumps operating on the first fluid line;
one or more pumps operating on the second fluid line;
one blood pump acting on the withdrawal line and one blood pump acting on the return line, said pumps being differentially operated,
one or more pumps operating both on the first and on the second fluid lines.

In a third aspect according to any one of the preceding aspects said at least one sensor comprises a first pressure sensor on the first fluid line and a second pressure sensor located either on the second fluid line or on the bloodline, both said first and second pressure sensor being connected to the control unit.

In a fourth aspect according to any one of the preceding aspects the receiving said pressure signals and determining a corresponding parameter value comprises:

receiving corresponding pressure signals from the pressure sensors and
estimating, based on said pressure signals, the value of the pressure drop across said auxiliary treatment unit.

In a fifth aspect according to the fourth aspect the controlling comprises controlling the flow regulator based on the pressure drop value.

In a sixth aspect according to any one of the preceding aspects the control procedure further comprises controlling the fluid flow regulator to keep said value of the pressure drop substantially constant over time.

In a seventh aspect according to any one of the preceding aspects the control procedure comprises a calibration phase including the following steps:

activating the flow regulator at different speeds,
detecting the actual flow rate through one of said first and second fluid lines at each respective speed, and
storing paired data comprising the speed of the flow regulator and the actual flow rate through the first or second fluid line at the respective speed,
calculating a characteristic curve from said paired data.

In an eighth aspect according to the seventh aspect the curves pump speed and actual flow rate are created at different pressure regimes, the apparatus includes a pressure sensor on the second fluid line which provides an indication of the pressure upstream the pump. In this case the control unit will store a plurality of calibration curves wherein, for each curve relating to a respective upstream pressure, the actual flow rate is function of the pump angular speed.

In a ninth aspect according to the seventh aspect or to the sixth aspect the control unit is configured to control the flow regulator based on a reference value of the flow rate through the first or second fluid lines and on the characteristic curve In a tenth aspect according to the ninth aspect, said controlling the flow regulator comprises activating the flow regulator at a speed selected to keep the difference between actual flow rate through the first or second fluid line and said reference value below a control threshold.

In an eleventh aspect according to any one of the preceding aspects the control procedure is periodically repeated.

In a twelfth aspect according to any one of the preceding aspects the auxiliary treatment unit comprises a semi-permeable membrane dividing said auxiliary unit into a first chamber and a second chamber, the fluid inlet communicating with the first chamber and the fluid outlet communicating with the second chamber of the auxiliary treatment unit such that fluid exiting out of the fluid outlet is ultrafiltered through the membrane.

In a thirteenth aspect according to the twelfth aspect said pressure drop value represents a transmembrane pressure across said semipermeable membrane of the auxiliary treatment unit.

In a fourteenth aspect according to any one of the preceding aspects the second fluid line has a first end connected to the fluid outlet of the auxiliary treatment unit and a second end directly connected to the blood withdrawal line or directly connected to the blood return line.

In a fifteenth aspect according to the preceding aspect the second fluid line is directly connected to the blood withdrawal line at a junction point located upstream or downstream a blood pump segment, and wherein said second pressure sensor is located on the blood withdrawal line in between a patient connection end and said junction point with the second fluid line.

In a sixteenth aspect according to any one of the preceding aspects the fluid flow regulator acts on said first fluid line.

In a seventeenth aspect according to any one of the preceding aspects the first fluid line comprises a deformable tubing and the fluid flow regulator comprises either a first peristaltic pump acting on a segment of the first fluid line or a membrane pump.

In an eighteenth aspect according to the fifteenth or sixteenth aspect the fluid flow regulator is at least one first peristaltic pump and wherein the control unit is configured to control the angular speed of the first peristaltic pump based on a reference value of the flow rate through the first fluid line and on the characteristic curve, said controlling the flow regulator comprising operating the first peristaltic pump at a speed selected to keep the difference between actual flow rate through the first fluid line and said reference value below a control threshold.

In a nineteenth aspect according to the eighteenth aspect said first pressure sensor is located on said first fluid line between the auxiliary treatment unit and the fluid flow regulator.

In a twentieth aspect according to any one of the preceding aspects the control procedure further comprises:

determining the value of the transmembrane pressure across the membrane of said auxiliary treatment unit, and
controlling the speed of rotation of the first peristaltic pump to keep substantially constant the value of said determined transmembrane pressure.

In a twenty-first aspect according to any one of the preceding aspects the first chamber of the auxiliary treatment unit includes a fluid outlet which is connected to an effluent fluid line.

In a twenty-second aspect according to the preceding aspect the effluent line connects the outlet of the first chamber of the auxiliary treatment unit to a drain or to a waste liquid container.

In a twenty-third aspect according to the preceding aspect the effluent line connects the outlet of the first chamber of the auxiliary treatment unit to a waste container positioned on a waste container scale detecting the weight of the waste container and sending a corresponding weight signal to the control unit.

In a twenty-fourth aspect according to the preceding aspect the control unit is configured for determining the actual flow rate through said first fluid line during said calibration phase using the weight signal from said waste container scale.

In a twenty-fifth aspect according to any one of the preceding aspects the apparatus comprises a bypass line connecting the first fluid line to the waste container and a commuting valve on the first fluid line for switching fluid connection of the first fluid line from a treatment condition, where the first fluid line is connected to the inlet of the auxiliary treatment unit, to a calibration condition, where the first treatment line is connected through the bypass line to the waste container.

In a twenty-sixth aspect according to any one of the preceding aspects the apparatus has a second flow regulator, optionally including a second peristaltic pump, operating on the effluent line.

In a twenty-seventh aspect according to the preceding aspect the control procedure further comprises controlling the second flow regulator based on the weight signal from the waste container scale and on a set flow rate value, optionally wherein the set flow rate value corresponds to a dose value the control unit is programmed to receive from a user.

In a twenty-eighth aspect according to any one of the preceding aspects the apparatus comprises a post-dilution line directly connected to the blood return line and to a first source of sterile replacement liquid.

In a twenty-ninth aspect according to any one of the preceding aspects the apparatus further comprises a pre-dilution line is directly connected to blood withdrawal line and to a second source of sterile replacement liquid.

In a thirtieth aspect according to any one of the preceding twenty-eighth and twenty-ninth aspects, the first source of sterile liquid is a first replacement fluid container, optionally a bag, of sterile liquid supported on a first replacement fluid scale configured to detect the first replacement fluid container weight and to send a corresponding weight signal to the control unit.

In a thirty-first aspect according to any one of the preceding twenty-eighth, twenty-ninth and thirtieth aspects the second source of sterile liquid is a second replacement fluid container, optionally a bag, of sterile liquid supported on a second replacement fluid scale configured to detect the second replacement fluid weight and to send a corresponding weight signal to the control unit.

In a thirty-second aspect according to any one of the preceding twenty-eighth, twenty-ninth, thirtieth, and thirty-first aspects wherein the control procedure further comprises:
 receiving the weight signal from said first and/or second replacement fluid scales,
 controlling a respective fluid regulator on said pre-dilution and/or on said post dilution line based on the corresponding weight signal from the replacement fluid scales and on a corresponding set value for an replacement fluid flow rate.

In a thirty-third aspect according to any one of the preceding aspects the molecular permeability of the membrane separating the main treatment unit in two compartments is greater than the molecular permeability of the membrane of the auxiliary treatment unit, at least above a certain molecular weight.

In a thirty-fourth aspect according to any one of the preceding aspects the membrane separating the main treatment unit in two compartments is a high-flux membrane.

In a thirty-fifth aspect according to any one of the preceding aspects from twelfth to thirty-fourth the difference in cut-off value between the membrane of the main treatment unit and the membrane of the auxiliary treatment unit lies between about 10,000 Daltons and 30,000 Daltons, optionally between about 10,000 Daltons and about 20,000 Daltons.

In a thirty-sixth aspect according to any one of the preceding aspects from twelfth to thirty-fifth the cut-off value of the membrane of the main treatment unit is equal to or less than about 40,000 Daltons.

In a thirty-seventh aspect according to any one of the preceding aspects from twelfth to thirty-sixth the cut-off value of the membrane of the main treatment unit is between about 20,000 Daltons and 40,000 Daltons.

In a thirty-eighth aspect according to any one of the preceding aspects from twelfth to thirty-seventh the cut-off value of the membrane of the auxiliary treatment unit is equal to or less than about 10,000 Daltons.

In a thirty-ninth aspect according to any one of the preceding aspects from twelfth to thirty-eighth the cut-off value of the membrane of the auxiliary treatment unit is between about 2,000 Daltons and about 10,000 Daltons.

In a fortieth aspect according to any one of the preceding aspects from twelfth to thirty-ninth the membrane of the main treatment unit is a plasma filter.

In a forty-first aspect according to the preceding aspect the plasma filter has a cut-off value between about one million Daltons and about five million Daltons, optionally between about two million Daltons and about three million Daltons.

In a forty-second aspect according to the thirty-ninth or fortieth aspect the auxiliary treatment unit comprises a unit selected from the group including: an adsorption cartridge, a reactor, a membrane separator having a cut off of about 80,000 Daltons, and a membrane separator having a cut off between about 60,000 Daltons and about 80,000 Daltons.

In a forty-third aspect according to any one of the preceding aspects the apparatus comprises a first treatment liquid line connecting a first source of treatment liquid to an inlet of the second chamber of the main treatment unit.

In a forty-fourth aspect according to any one of the preceding aspects from the twelfth to the forty-third the apparatus comprises a second treatment liquid line connecting a second source of treatment liquid to an inlet of the second chamber of the auxiliary treatment unit.

A forty-fifth aspect relates to a process for controlling an extracorporeal blood treatment apparatus, the apparatus having the features of any one of the preceding aspects.

In a forty-sixth aspect according to the forty-fifth aspect the process comprises:
 receiving said pressure signal from the sensing means and determining a corresponding parameter value, and
 controlling the flow regulator at least based on said parameter value.

In a forty-seventh according to any one of the preceding aspects forty-fifth or forty-sixth the receiving said pressure signals and determining a corresponding parameter value comprises:
 receiving corresponding pressure signals from each of first and second pressure sensors, of the sensing means and
 estimating, based on said pressure signals, the value of the pressure drop across said auxiliary treatment unit.

In a forty-eighth aspect according to the forty-seventh aspect the controlling comprises controlling the flow regulator based on the pressure drop value.

In a forty-ninth aspect according to any one of the preceding aspects from forty-fifth to forty-eighth the process further comprises controlling the fluid flow regulator such as to keep said value of the pressure drop substantially constant over time.

In a fiftieth aspect according to any one of aspects from the forty-fifth to the forty-ninth, the process includes periodically executing a first control procedure including:
  receiving corresponding pressure signals from each of said first and second pressure sensors,
  estimating, based on said pressure signals, the value of pressure drop across said auxiliary treatment unit,
  controlling the flow regulator based on the pressure drop value to keep said value of the pressure drop substantially constant over time or to keep a difference between the pressure drop value and a reference value below a set threshold.

In a fifty-first aspect according to the fiftieth aspect the process includes a calibration phase comprising:
  activating the flow regulator at different speeds,
  detecting the actual flow rate through one of said first and second fluid lines at each respective speed, and
  storing pairs each comprising the speed of the flow regulator and the actual flow rate through the first or second fluid line at the respective speed,
  calculating a characteristic curve from said pairs, optionally wherein the calibration phase is executed before executing said first control procedure.

In a fifty-second aspect according to the fifty-first aspect the process includes executing a second control procedure comprising periodically controlling the flow regulator based on a reference value of the flow rate through the first or second fluid lines and on the characteristic curve.

In a fifty-third aspect according to the fifty-second aspect said controlling the flow regulator comprises activating the flow regulator at a speed that makes the difference between actual flow rate through the first or second fluid line and said reference value below a control threshold.

In a fifty-fourth aspect according to the fifty-second or the fifty-third aspect the second control procedure is executed during intervals when the first control procedure is not executed, optionally wherein the two control procedures are alternated over time.

In a fifty-fifth aspect according to any one of aspects from the forty-fifth to the fifty-fourth:
  the auxiliary treatment unit comprises a semi-permeable membrane dividing said auxiliary unit into a first chamber and a second chamber, the fluid inlet communicating with the first chamber and the fluid outlet communicating with the second chamber of the auxiliary treatment unit such that fluid exiting out of the fluid outlet is ultrafiltered through the membrane,
  said pressure drop value represents a trans membrane pressure across said semipermeable membrane of the auxiliary treatment unit,
  said first pressure sensor is located on said first fluid line between the auxiliary treatment unit and the fluid flow regulator,
and wherein:
  estimating the value of pressure drop across said auxiliary treatment unit comprises
    determining the value of the transmembrane pressure across the membrane of said auxiliary treatment unit, and
    controlling the flow regulator comprises controlling the speed of rotation of the first peristaltic pump to keep substantially constant the value of said determined transmembrane pressure or to keep a difference between the transmembrane value and a reference value below a set threshold.

In a fifty-sixth aspect according to any one of aspects from the forty-fifth to the fifty-fifth aspects:
  the fluid flow regulator acts on said first fluid line,
  the first fluid line comprises a deformable tubing,
  the fluid flow regulator comprises a first peristaltic pump and
  wherein the process comprises controlling the angular speed of the first peristaltic pump based on a reference value of the flow rate through the first fluid line and on the characteristic curve, said controlling the flow regulator comprising turning the first peristaltic pump at a speed that makes the difference between actual flow rate through the first fluid line and said reference value below a control threshold.

The above summary is not intended to describe each embodiment or every implementation of the apparatus and methods described herein. Rather, a more complete understanding of the invention will become apparent and appreciated by reference to the following Detailed Description and claims in view of the accompanying figures of the drawing.

BRIEF DESCRIPTION OF THE DRAWINGS

The attached drawings disclose exemplifying and non-limiting aspects of some embodiments of the apparatus described herein, wherein.

DETAILED DESCRIPTION

Figure 1:
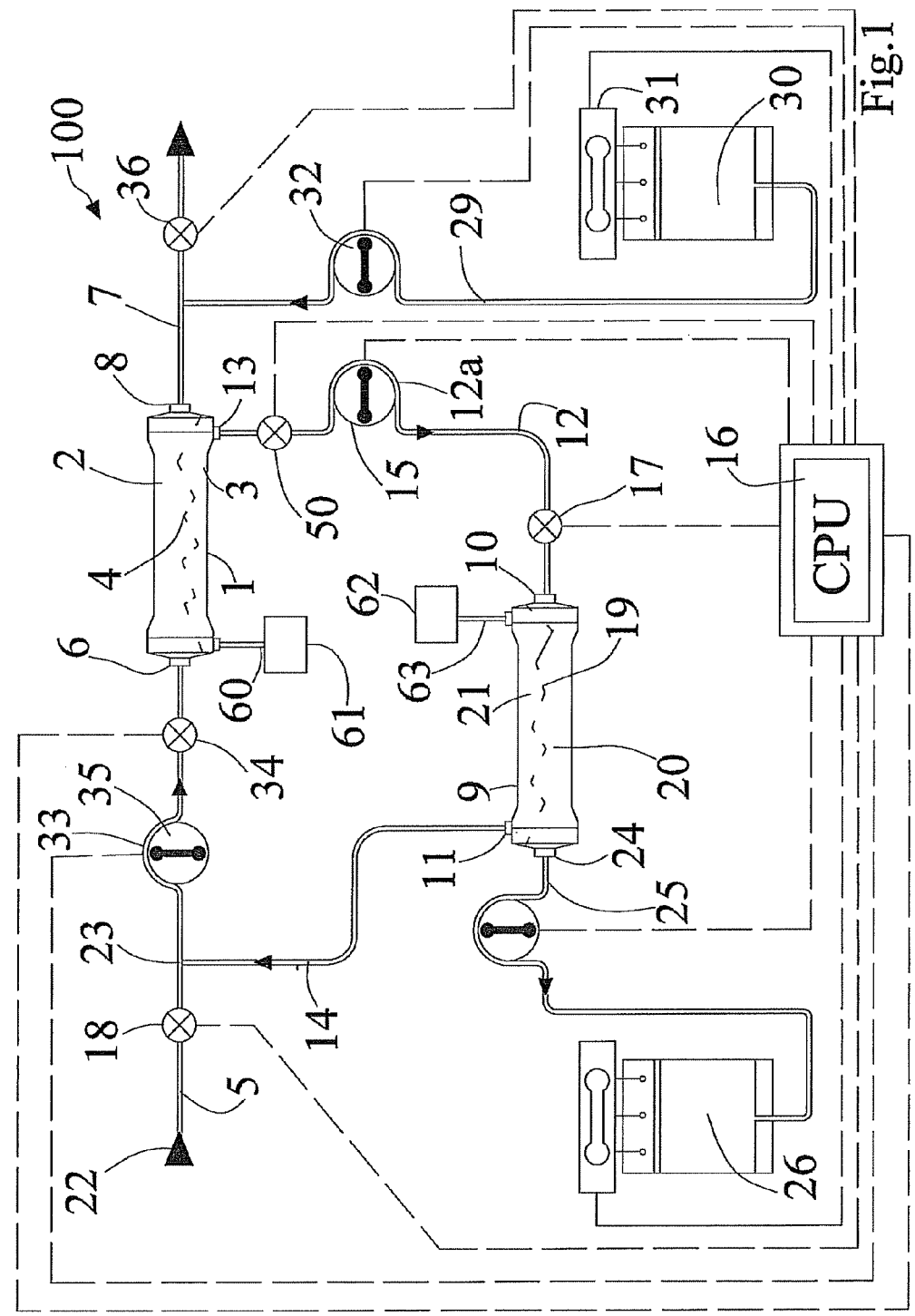
FIG. 1 is a schematic diagram of a first fluid circuit of one embodiment of a blood treatment apparatus as described herein.

In the following description of illustrative embodiments, reference is made to the accompanying figures of the drawing which form a part hereof, and in which are shown, by way of illustration, specific embodiments. It is to be understood that other embodiments may be utilized and structural changes may be made without departing from the scope of the present invention.

With reference to the enclosed drawings, reference numeral 100 indicates an extra-corporeal blood treatment apparatus which can be used for the treatment of blood with the aim of removing undesired solutes from patient blood.

The apparatus 100 comprises at least a main treatment unit 1 (e.g. a dialyzer or an hemofilter or an hemodiafilter or a plasmafilter) having a first compartment 2 and a second compartment 3 separated by a semipermeable membrane 4.

The semipermeable membrane 4 can be, e.g., a hollow fibers membrane or a plate membrane and allows a selective filtration of blood. In case of hollow membranes, blood typically flows through the membrane cavities which define the first compartment. In order to connect the first compartment 2 with the patient's vascular system the apparatus comprises a blood withdrawal line 5 for blood to be treated having one end connected to an inlet 6 of the first compartment 2 of the main treatment unit 1 and another end connectable to an access device such as for example a needle a catheter, or an implanted port. A blood return line 7 is connected, at one of its ends, to an outlet 8 of the first compartment 2 of the main treatment unit 1 and, at the other of its ends, to an access device such as for example a needle, a catheter, or an implanted port. In practice, the blood return line, the blood withdrawal line and the first compartment are part of an extracorporeal blood circuit which is used to circulate patient's blood outside the patient vascular system and to return the blood after this latter has been treated.

The apparatus 100 also includes at least an auxiliary treatment unit 9 (for instance one, two or more auxiliary treatment units connected in series or in parallel could be used) comprising at least one fluid inlet 10 and at least one fluid outlet 11. More in detail, a first fluid line 12 has a first end connected to an outlet 13 of the second compartment 3 of the main treatment unit 1 and a second end connected to the fluid inlet 10 of the auxiliary treatment unit 9, so that fluid ultrafiltered through the membrane 4 exits outlet 13 and enters into fluid inlet 10 to then be treated by the auxiliary treatment unit 9. A second fluid line 14 has a first end connected to the fluid outlet 11 of the auxiliary treatment unit 9 and a second end which can be either connected to the blood withdrawal line 5 (FIG. 1) or to the blood return line 7 (FIG. 2) of the extracorporeal blood circuit. Although this is not shown in the drawings, as a further alternative, the second fluid line could also be connected directly to the blood withdrawal line at a point located between the blood pump 35 and the main treatment unit 1.

The apparatus also includes a fluid flow regulator 15 on at least one of said first and second fluid lines 12, 14. The fluid flow regulator may comprise at least one pump. For instance in FIGS. 1 and 2 a fluid flow regulator 15 is depicted in the form of a first peristaltic pump placed on the first fluid line 12. The first fluid line is in this case a deformable tubing and the first peristaltic pump acts on a tube segment 12a of the first fluid line. Alternatively, in place of the first peristaltic pump a membrane pump, diaphragm pump, etc. could be used.

A control unit 16 is also part of the apparatus 100 and can be either a programmable digital unit (CPU) of an analogical type control device or a combination thereof. For example the control unit can include one or more digital microprocessors provided with one of more memories and operatively connected to the one or more sensors and actuators in order to coordinate operation of the blood treatment apparatus at it will be here-below described in greater detail.

Figure 2:
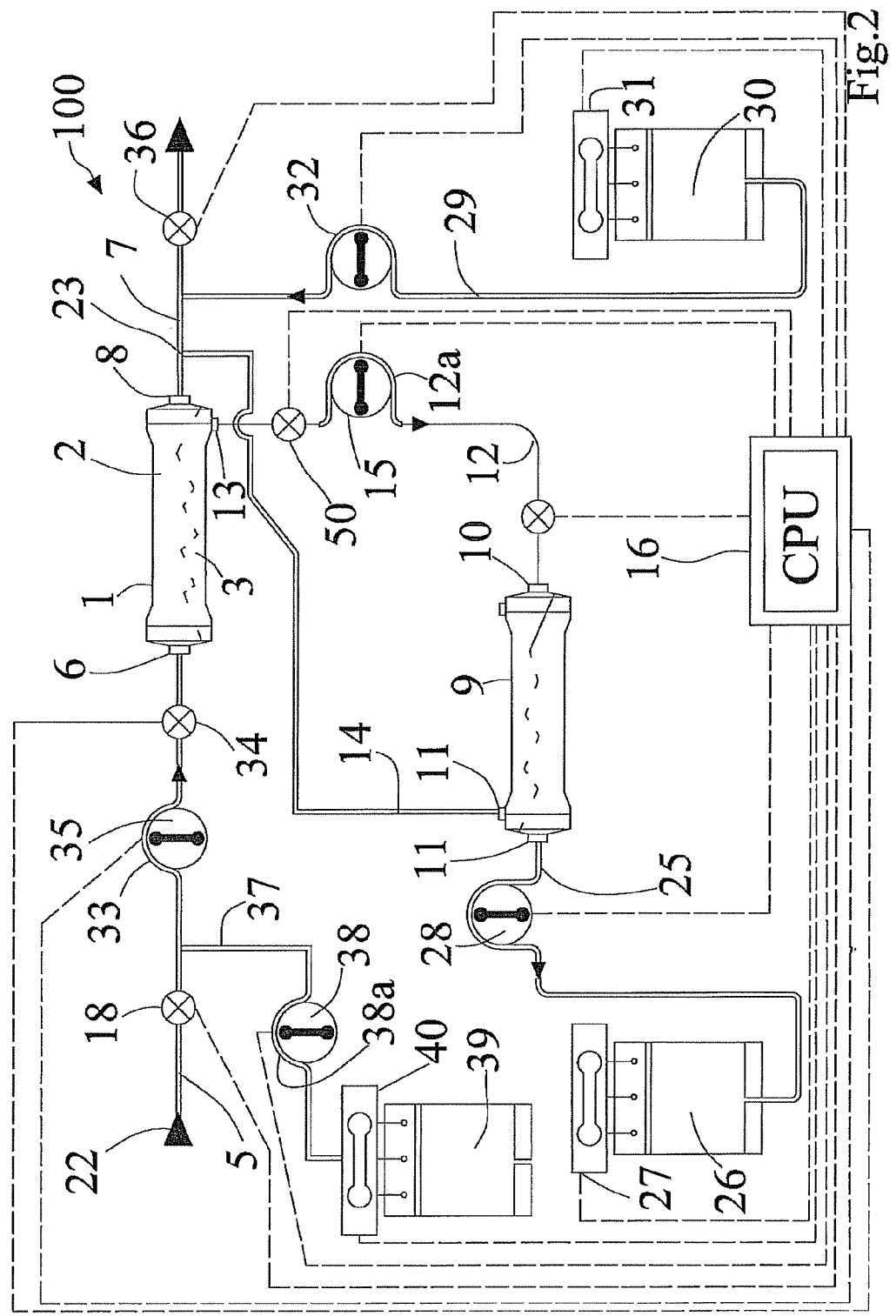
FIG. 2 is schematic diagram of a second fluid circuit of one embodiment of a blood treatment apparatus as described herein.

The apparatus includes at least one sensor connected to the control unit 16 for determining a parameter related to a pressure drop across said auxiliary treatment unit and emitting a corresponding pressure signal which is sent to the control unit 16. The control unit 16 is configured (for instance the control unit can execute one or more instructions stored in the memory associated with the control unit) to execute a specific control procedure allowing to keep the actual flow of fluid through line 12 under control. The control procedure executed by the control unit 16 comprises receiving the pressure signal from the sensor, determining a corresponding parameter value, and controlling the flow regulator 15 at least based on said parameter value. In practice the actual speed of rotation of the peristaltic pump 15 is controlled based on the pressure signal from the mentioned sensor or sensors. As shown in FIGS. 1 and 2 in order to detect the pressure drop across the auxiliary treatment unit 9, two sensors are provided: a first pressure sensor 17 on the first fluid line and a second pressure sensor 18 located either on the second fluid line or directly on the bloodline; both said first and second pressure sensors are connected to the control unit which can determine the pressure drop across the auxiliary treatment unit 9 based on the pressure signals coming from the first and second sensors. In this respect, the control unit is configured to execute a control procedure comprising: receiving corresponding pressure signals from each of said first and second pressure sensors 17, 18, estimating, based on said pressure signals, the value of the pressure drop across said auxiliary treatment unit 9, and controlling the flow regulator 15 based on the pressure drop value.

In the examples of FIGS. 1-4 the auxiliary treatment unit 9 is a filter of the type which comprises a semi-permeable membrane 19 dividing the auxiliary unit into a first chamber 20 and a second chamber 21. The fluid inlet 10 communicates with the first chamber and supplies to the first chamber the fluid ultrafiltered through the membrane 4 of the main treatment unit 1, while the fluid outlet 11 communicates with the second chamber 21 of the auxiliary treatment unit such that fluid exiting out of the fluid outlet 11 is ultrafiltered through the membrane 19. In this case the pressure drop determined by the above sensors is referred to as transmembrane pressure (TMP) across the membrane of the auxiliary treatment unit. According to an aspect, the control procedure executed by the control unit comprises controlling the fluid flow regulator 15 such as to keep said value of the pressure drop (or TMP) substantially equal to a set or settable reference value which can be constant over time or can correspond to a selected profile.

Figure 3:
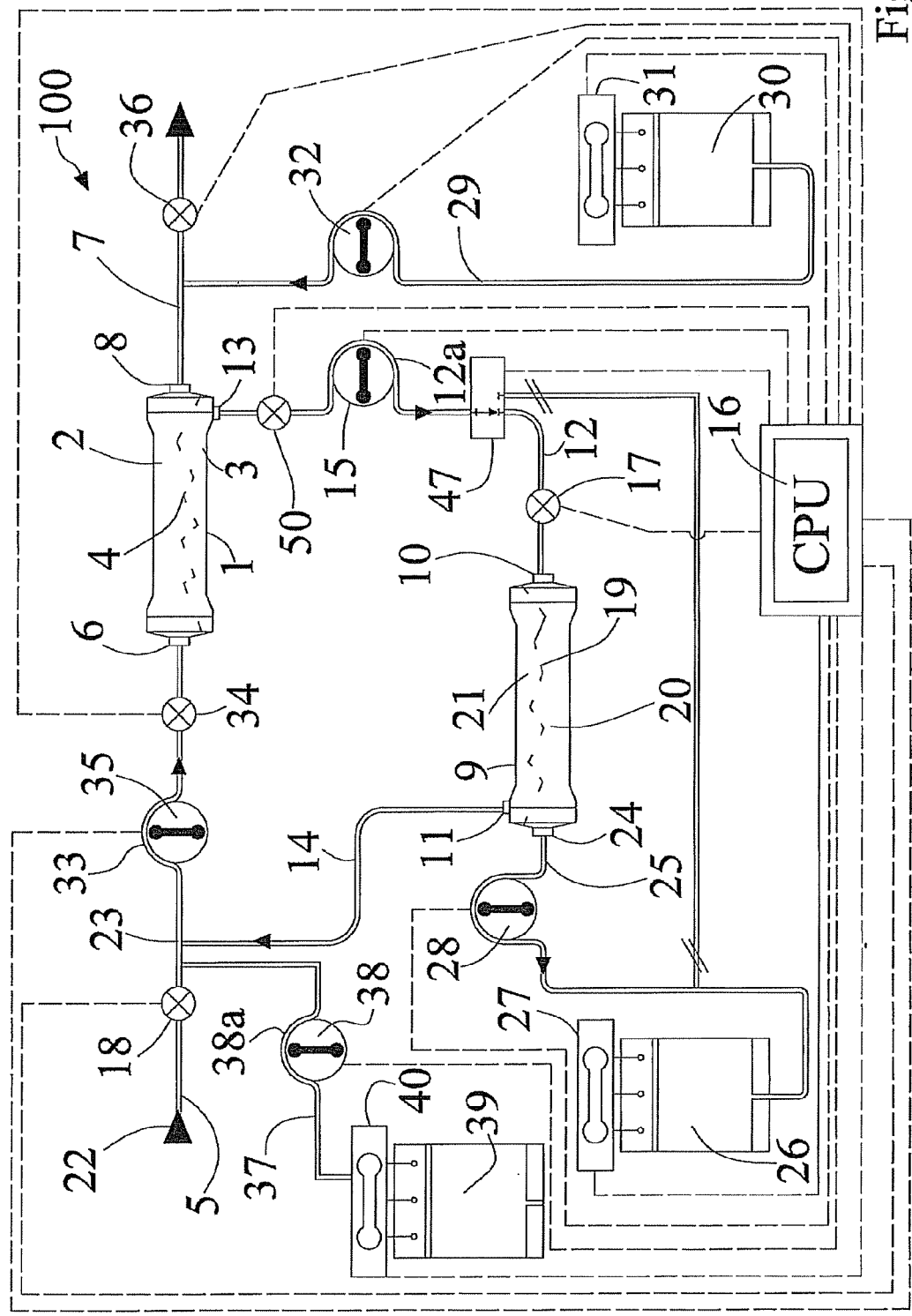
FIG. 3 is schematic diagram of a third fluid circuit of one embodiment of a blood treatment apparatus as described herein, where a valve is present to shift the circuit from a running treatment mode to a calibration mode.

In other words, referring to the examples in FIGS. 1-3, the speed of the ultrafiltration pump is controlled such as the measured TMP across the auxiliary unit follows a selected profile or is equal to a known preselected constant value.

In the example of FIG. 1, the second fluid line 14 has a first end connected to the fluid outlet 11 of the auxiliary treatment unit 9 and a second end directly connected to the blood withdrawal line, in correspondence of a junction point 23 which is located between the second pressure sensor 18 of the blood withdrawal line and the pump segment 33 of the same blood withdrawal line. Note that pump segment 33 is supposed to cooperate with a peristaltic blood pump 35 which in use acts on the pump segment 33 to move blood from the access into the first chamber 2 of the main treatment unit 1. The second pressure sensor 18 is located on the blood withdrawal line 5 in between a patient connection end 22 and the junction point 23 with the second fluid line 14. Alternatively the pressure sensor 18 could be located on line 5 between the junction point 23 and the blood pump 35.

In the example of FIG. 2, the various components are configured as in FIG. 1, but for the second fluid line 14 which has a first end connected to the fluid outlet 11 of the auxiliary treatment unit 9 and a second end directly connected to the blood return line 7, in correspondence of a junction point 23 which is located downstream the outlet 8, but upstream of outlet pressure sensor 36.

In both embodiments of FIGS. 1 and 2, the first pressure sensor 17 is located on said first fluid line 12 between the auxiliary treatment unit 9 and the fluid flow regulator 15.

Moreover, in both embodiments (this should not however be considered as a limiting aspect), an inlet pressure sensor 34 is located on the blood withdrawal line immediately upstream the blood treatment unit 1 and an outlet pressure sensor 36 is located on the blood return line immediately downstream the blood treatment unit 1. A further pressure sensor 50 may be positioned on line 12 between the flow regulator 15 and outlet 13. Using the signals from one or more of the pressure sensors, e.g. from pressure sensors 17 and 18, or 17 and 34, or 17, 18 and 34 above described, the control unit 16 can determine the value of the transmembrane pressure across the membrane of said auxiliary treatment unit 9, and can control the speed of rotation of the first peristaltic pump 15 to keep substantially constant the value of said determined transmembrane pressure.

In accordance with a further aspect, as shown in the examples of FIGS. 1-4, the first chamber of the auxiliary treatment unit 9 includes a fluid outlet 24 connected to an effluent fluid line 25 leading to a drain or to a waste liquid container 26. In the examples shown the flow rate through the fluid line 25 is kept under accurate control. In the depicted embodiment, the effluent line 25 connects the outlet of the first chamber of the auxiliary treatment unit to a waste container 26 positioned on a waste container scale 27 detecting the weight (or at least the weight change) of the waste container and sending a corresponding weight signal to the control unit.

A second flow regulator 28, for instance a second peristaltic pump, operates on the effluent line 25 under the control of control unit 16. This latter is configured to control the second flow regulator based on the weight signal from the waste container scale and on a set flow rate value, such that the flow rate through line 25 and thereby the rate of fluid removed from the blood is kept corresponding to a set dose value (e.g. a constant flow rate) the control unit is programmed to receive from a user or to read from a memory. In other words the control unit is configured to control the speed of the ultrafiltration pump such as to keep the TMP across the auxiliary unit constant and at the same time to keep the flow rate to the waste container also under precise control (e.g. constant) by using the signals from scale 27.

Going back to FIGS. 1 and 2, it is possible to note that the apparatus 100 may further include a post-dilution line 29 connected to the blood return line 7 and to a first source of sterile replacement liquid 30. In practice, this latter may comprise a replacement bag supported by a respective holding structure. Moreover, a scale 31 or other weighting sensor may be placed in order to detect the weight of the replacement bag or at least the changing weight of said replacement bag to then send a corresponding signal or to the control unit 16 which, in turn, may control the replacement pump 32. The apparatus 100 may also include a pre-dilution line 37 (see, e.g., the example of FIGS. 2-4) directly connected to the blood withdrawal line and to a second source of sterile replacement fluid 39. Also the pre-dilution line 37 includes a pump segment 38*a* cooperating with a peristaltic pump 38 and is designed to move fluid coming from the second source of sterile replacement liquid, for instance a bag 39 which is supported by a respective holding structure and which may cooperate with a respective weight sensor 40 capable of detecting the weight of bag 39 or at least the change in weight of this latter. A corresponding weight signal is issued by the scale 40 and is sent to the control unit 16 which, based on said weight signal, is configured to control the peristaltic pump 38.

In other words, the control unit, in addition to the functions described above, may also be configured to receive the signal from the first and the second replacement fluid scales and for controlling a respective fluid regulator 32, 38 located on each of said pre-dilution and post-dilution line based on the corresponding weight signal issued by the respectively placed fluid scales and on a set value for the replacement fluid flow rate that should circulate along the replacement fluid lines 29 and 37.

Main and Auxiliary Treatment Units

Above a certain molecular size, the molecular permeability of the membrane 4 of the main treatment unit is greater than the molecular permeability of the membrane 19 of the auxiliary treatment unit. This in combination with the specific design of the circuit of apparatus 100 allows for selective removal of specific particles of a certain size range.

Figure 5:
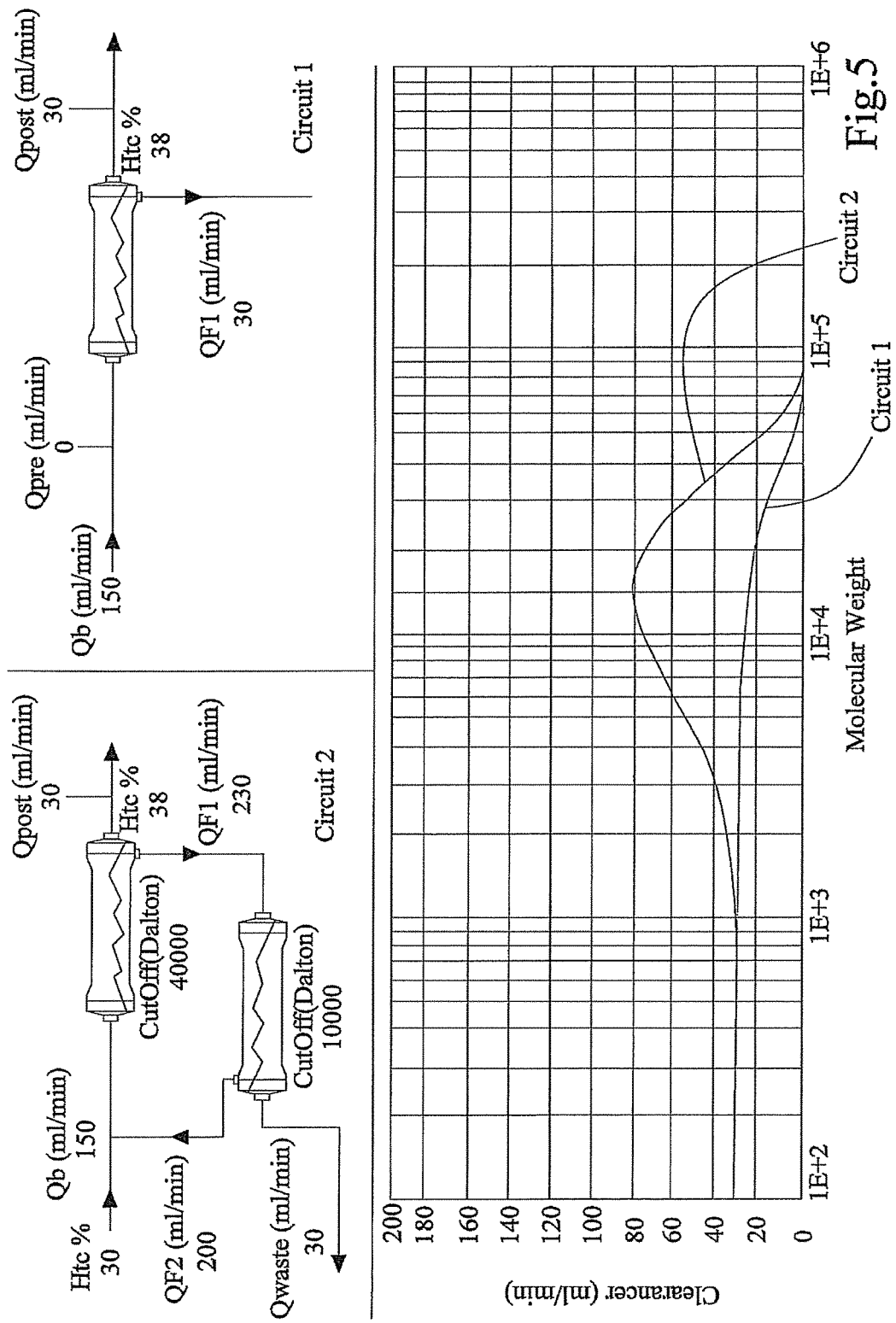
FIG. 5 is a diagram showing the characteristic curves of the main treatment unit and of the auxiliary treatment unit in one example of implementation (circuit 2) compared to a conventional hemofiltration circuit (circuit 1).

For instance, referring to the examples of FIGS. 1 and 2, the difference in cut-off value between the membrane of the main treatment unit and the membrane of the auxiliary treatment unit lies between about 10,000 Daltons and about 30,000 Daltons. In one example, the cut-off value of the membrane 4 of the main treatment unit may be equal or less than about 40,000 Daltons. As to the membrane of the auxiliary treatment unit, the cut-off value of this membrane is equal or less than about 10,000 Daltons. For instance, the main treatment unit may present a membrane having a cut-off value comprised between about 20,000 Daltons and about 40,000 Daltons while the cut-off value of the membrane of the auxiliary treatment unit lies between about 2,000 Daltons and about 10,000 Daltons. In other words the membrane of the auxiliary treatment unit can be selective to small-sized molecules, while the membrane of the main treatment unit can be up to medium-sized molecules. FIG. 5 shows a schematic of a circuit (referred to as circuit 2 in FIG. 5) and the respective clearance curve in a situation where the cutoff of the main treatment unit is about 40,000 Daltons while that of the auxiliary treatment unit is about 10,000 Daltons. The clearance curve of circuit 2 is compared to the clearance curve of a conventional hemofiltration circuit (referred to as circuit 1 in FIG. 5) in order to show how the present embodiments can accentuate clearance on mid-sized particles.

In accordance with other embodiments the main treatment unit can be a plasma filter, with a cut-off value between about 1,000,000 Daltons and about 5,000,000 Daltons. In this case the auxiliary treatment unit may comprise a unit selected from the following: absorption cartridge, a reactor, a membrane separator with a cut-off of about 80,000 Daltons, or a membrane separator having a cut-off between about 60,000 Daltons and about 80,000 Daltons.

Finally, although this should not be interpreted as a limitation, it is also possible to provide the apparatus 100 with a further liquid line 60 connecting a first source 61 of dialysis treatment liquid to an inlet of the second chamber 13 of the main treatment unit, in order to remove the particles not only by a convection, but also through diffusion due to a concentration gradient between the liquid coming from the source and blood. It may also be possible to have a second source of dialysis treatment liquid 62 and a corresponding second liquid line 63 connecting the second source 62 to an inlet of the second chamber 21 of the auxiliary treatment unit: in this case the auxiliary treatment unit is of the type having a membrane defining the two chambers in the auxiliary treatment unit. The liquid coming from the second source allows to remove particles by diffusion and not only by convection. Note that (as for those examples of apparatus 100 where no dialysis lines 60 or 63 are present) also in those cases where apparatus 100 includes one or more dialysis lines are connected to the second chamber of the main treatment unit or to the second chamber of the auxiliary treatment unit, apparatus 100 may also include further treatment units: for instance further auxiliary treatment units could be connected in parallel or in series to the auxiliary treatment unit 19.

Start Up and Calibration Procedure

Figure 4:
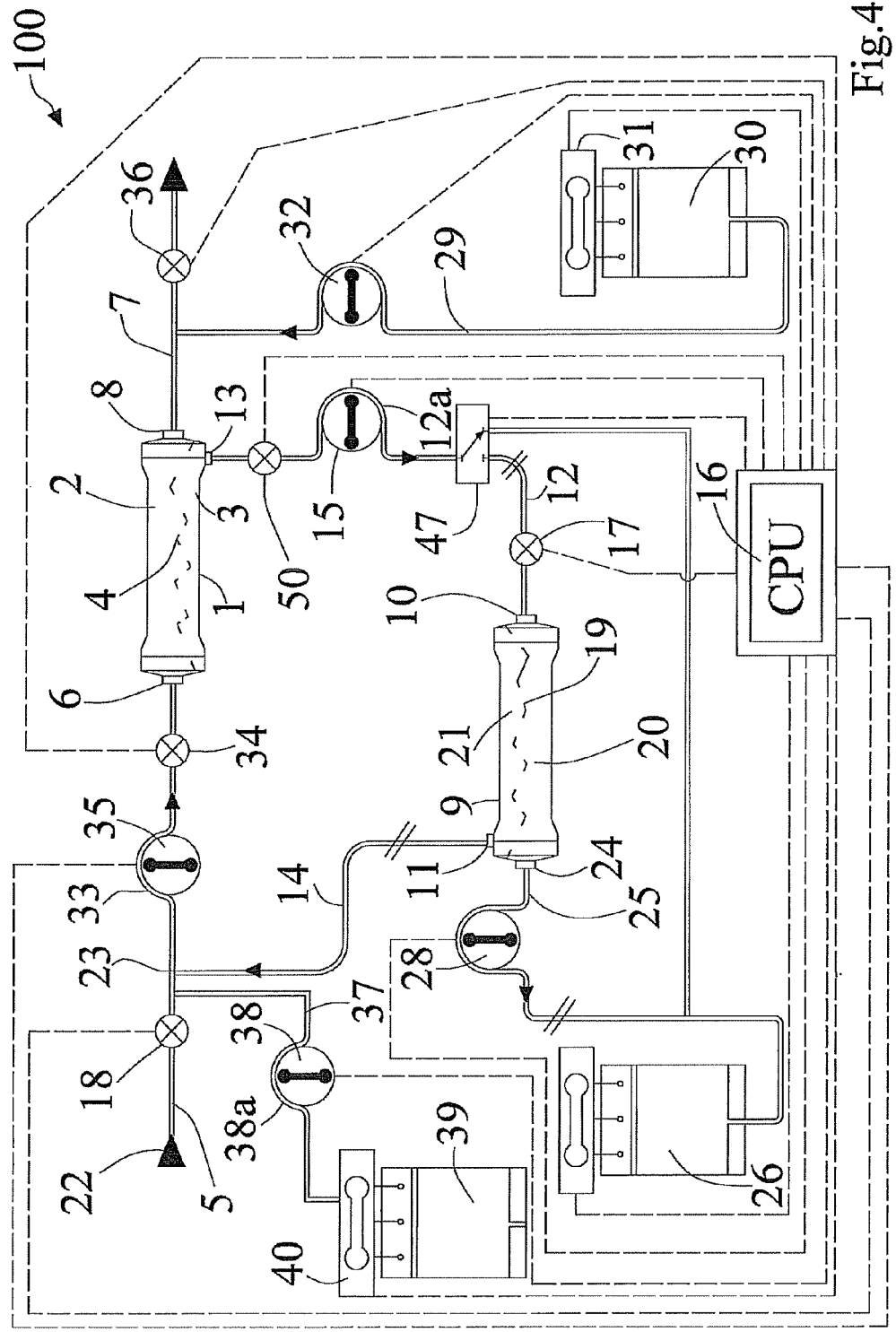
FIG. 4 is schematic diagram of the circuit of FIG. 3 in calibration mode.

With reference to FIGS. 3 and 4, it is shown that the device may also include a commuting valve 47 which is able to bypass the auxiliary treatment unit. The commutation can be done either manually or by an appropriate command coming from the control unit 16.

The control unit is configured to execute a calibration procedure in order to determine a characteristic curve establishing a relationship between the number of turns of the pump and the actual flow rate flowing through line 12 when this latter bypasses the auxiliary treatment unit and is directly connected to the effluent bag. In practice, when the calibration procedure is started, the control unit or the user switches the commuting valve to bypass mode. In bypass mode, the effluent weight scale 27 provides the control unit with a weight signal which serves to determine the actual flow rate through line 12. The control unit is then configured to activate the ultra-filtration pump at different angular speeds and to build a series of paired data (number of turns of pump 15, actual flow rate) relating the angular speed of the pump and the actual flow rate through the line 12. The control unit stores the paired data and calculates a characteristic curve (e.g. by curve fitting). It should be noted that the actual flow rate of a peristaltic pump is mainly dependent on both pump speed and upstream pressure as the upstream pressure directly acts on the profile of the cross section of the pump segment which decreases with decreasing upstream pressure.

In this sense, for a given pump speed, the actual flow rate will vary if the upstream pressure varies. Therefore, the curves for pump speed and actual flow rate can be created at different pressure regimes as the apparatus 100 includes pressure sensor 50 which can also provide an indication of the pressure upstream the pump 15. In this last case the control unit will store a plurality of calibration curves wherein, for each curve relating to a respective upstream pressure, the actual flow rate is function of the pump angular speed.

It should also be noted that the calibration procedure may also comprise one of:
  Waiting a preselected time after start of the calibration procedure and before start of storing of said series of paired data (optionally a respective series of paired data for each value of upstream pressure as above explained), or
  Detecting the temperature of the fluid circulating in one of lines 12 or 25 and wait until the temperature has sufficiently stabilized before storing of the paired data used for building the calibration curves.

A further aspect that can also be featured by the apparatus 100 comprises, during the calibration procedure, infusing a replacement fluid in predilution in order to avoid hemoconcentration in the main membrane. Indeed, during bypass, the ultrafiltrate from the auxiliary membrane is stopped and may preferably be compensated for in order keep the main membrane conditions unchanged.

The characteristic curve or curves is/are used during treatment for controlling the ultrafiltration pump speed.

For instance the control unit can be programmed to: execute the above described calibration procedure (before treatment and optionally also during treatment at certain time intervals) and build up a number of characteristic curves relating the angular speed of the pump 15 and the actual flow rate through line 12 at various pressure regimes, periodically control (during treatment) the pump 15 based on a set or reference value of the ultrafiltration flow rate and on the appropriate characteristic curve such as to turn the pump at a speed that may minimize the difference between actual flow rate and set or reference value, and periodically control (during treatment) the pump 15 such that the transmembrane pressure across the second treatment unit follows a reference value, which can be a constant value or a preselected profile (as above described).

Illustrative embodiments of the apparatus and methods are discussed and reference has been made to possible variations. These and other variations and modifications in the invention will be apparent to those skilled in the art without departing from the scope of the invention, and it should be understood that this invention is not limited to the illustrative embodiments set forth herein.

Accordingly, the invention is to be limited only by the claims provided below and equivalents thereof.

The invention claimed is:

1. An extracorporeal blood treatment apparatus comprising:
  at least a main treatment unit comprising a first compartment and a second compartment separated by a semipermeable membrane,
  a blood withdrawal line for blood to be treated connected to an inlet of the first compartment of the main treatment unit,
  a blood return line connected to an outlet of the first compartment of the main treatment unit, wherein the blood return line, the blood withdrawal line and the first compartment are part of an extracorporeal blood circuit,
  at least an auxiliary treatment unit comprising at least one fluid inlet and at least one fluid outlet, wherein the auxiliary treatment unit comprises a semipermeable membrane dividing said auxiliary treatment unit into a first chamber and a second chamber, the at least one fluid inlet communicating with the first chamber and the at least one fluid outlet communicating with the second chamber, wherein at least a portion of fluid entering the first chamber passes through the semipermeable membrane into the second chamber and exits the second chamber through the at least one fluid outlet,
  a first fluid line having a first end connected to an outlet of the second compartment of the main treatment unit and a second end connected to the fluid inlet of the auxiliary treatment unit,
  a second fluid line having a first end connected to the fluid outlet of the auxiliary treatment unit and a second end connected to said extracorporeal blood circuit,
  a fluid flow regulator on at least one of said first and second fluid lines,
  at least one sensor for determining a parameter related to a pressure drop across said auxiliary treatment unit and emitting a corresponding pressure signal, wherein said pressure drop represents a transmembrane pressure across said semipermeable membrane of the auxiliary treatment unit, and a control unit configured to execute a control procedure for a treatment time for a single patient that comprises:
receiving said pressure signal from the sensor and determining a corresponding parameter value, and
controlling the flow regulator at least based on said parameter value and to keep said value of the pressure drop across said auxiliary treatment unit substantially constant throughout the treatment time,
wherein the molecular permeability of the membrane of the main treatment unit is greater than the molecular permeability of the membrane of the auxiliary treatment unit,
wherein the difference in cut-off value between the membrane of the main treatment unit and the membrane of the auxiliary treatment unit lies between about 10,000 Daltons and about 30,000 Daltons.

2. An apparatus according to claim 1, wherein said at least one sensor comprises a first pressure sensor on the first fluid line and a second pressure sensor located either on the second fluid line or on the blood withdrawal line, both said first and second pressure sensor being connected to the control unit, and wherein the receiving said pressure signals and determining a corresponding parameter value comprises:
receiving corresponding pressure signals from each of said first and second pressure sensors, and
estimating, based on said pressure signals, the value of the pressure drop across said auxiliary treatment unit,
and wherein controlling the fluid flow regulator comprises controlling the fluid flow regulator based on the pressure drop value.

3. An apparatus according to claim 1, wherein the control procedure comprises a calibration phase that comprises:
activating the fluid flow regulator at different speeds,
detecting actual flow rate through one of said first and second fluid lines at each respective speed, and
storing paired data comprising the speed of the fluid flow regulator and the actual flow rate through the first or second fluid line at the respective speed,
calculating a characteristic curve from said paired data;
and wherein the control unit is configured to control the fluid flow regulator based on a reference value of the flow rate through the first or second fluid lines and on the characteristic curve, said controlling the fluid flow regulator comprising activating the fluid flow regulator at a speed selected to keep the difference between actual flow rate through the first or second fluid line and said reference value below a control threshold.

4. An apparatus according to claim 2, wherein the second fluid line has a first end connected to the fluid outlet of the auxiliary treatment unit and a second end directly connected to the blood withdrawal line.

5. An apparatus according to claim 4, wherein the second fluid line has the second end directly connected to the blood withdrawal line at a junction point located upstream or downstream a blood pump segment, and wherein a second pressure sensor is located on the blood withdrawal line in between a patient connection end and said junction point with the second fluid line.

6. An apparatus according to claim 1, wherein the fluid flow regulator acts on said first fluid line and wherein the first fluid line comprises a deformable tubing and the fluid flow regulator comprises a first peristaltic pump acting on a segment of the first fluid line.

7. An apparatus according to claim 3, wherein the fluid flow regulator acts on said first fluid line and wherein the first fluid line comprises a deformable tubing and the fluid flow regulator comprises a first peristaltic pump acting on a segment of the first fluid line, and further wherein the control unit is configured to control the angular speed of the first peristaltic pump based on a reference value of the flow rate through the first fluid line and on the characteristic curve, said controlling the fluid flow regulator comprising operating the first peristaltic pump at a speed selected to keep the difference between actual flow rate through the first fluid line and said reference value below a control threshold.

8. An apparatus according to claim 7, wherein said first pressure sensor is located on said first fluid line between the auxiliary treatment unit and the fluid flow regulator.

9. An apparatus according to claim 7, wherein the control procedure further comprises:
determining the value of the transmembrane pressure across the membrane of said auxiliary treatment unit, and
controlling the speed of rotation of the first peristaltic pump to keep the value of said determined transmembrane pressure substantially constant.

10. An apparatus according to claim 1, wherein the first chamber of the auxiliary treatment unit includes a fluid outlet which is connected to an effluent fluid line, wherein the effluent line connects the outlet of the first chamber of the auxiliary treatment unit to a drain or to a waste liquid container positioned on a waste container scale detecting the weight of the waste liquid container and sending a corresponding weight signal to the control unit.

11. An apparatus according to claim 10, wherein the control unit is configured to determine actual flow rate through said first fluid line during a calibration phase using the weight signal from said waste container scale.

12. An apparatus according to claim 10, comprising a bypass line connecting the first fluid line to the waste container and a commuting valve on the first fluid line for switching fluid connection of the first fluid line from a treatment condition, where the first fluid line is connected to the inlet of the auxiliary treatment unit, to a calibration condition, where the first fluid line is connected through the bypass line to the waste container.

13. An apparatus according to claim 10, wherein a second flow regulator operates on the effluent line and wherein the control procedure further comprises controlling the second flow regulator based on the weight signal from the waste container scale and on a set flow rate value, wherein the set flow rate value corresponds to a dose value the control unit is programmed to receive from a user.

14. An apparatus according to claim 1, further comprising a post-dilution line directly connected to the blood return line and to a first source of sterile replacement liquid or a pre-dilution line directly connected to the blood withdrawal line and to a second source of sterile replacement liquid.

15. An apparatus according to claim 1 further comprising a post-dilution line directly connected to the blood return line and to a first source of sterile replacement liquid and a pre-dilution line directly connected to the blood withdrawal line and to a second source of sterile replacement liquid, further wherein the first source of sterile liquid is a first replacement fluid container of sterile liquid supported on a first replacement fluid scale configured to detect the first replacement fluid container weight and to send a corresponding weight signal to the control unit, and wherein the second source of sterile liquid is a second replacement fluid container of sterile liquid supported on a second replacement fluid scale configured to detect the second replacement fluid weight and to send a corresponding weight signal to the control unit.

16. An apparatus according to claim 15, wherein the control procedure further comprises:
  receiving the weight signal from said first and second replacement fluid scales,
  controlling a respective fluid regulator on said pre-dilution and/or on said post dilution line based on the corresponding weight signal from the replacement fluid scales and on a corresponding set value for an replacement fluid flow rate.

17. An apparatus according to claim 1,
  wherein the cut-off value of the membrane of the main treatment unit is equal to or less than about 40,000 Daltons, and
  wherein the cut-off value of the membrane of the auxiliary treatment unit is equal to or less than about 10,000 Daltons.

18. An apparatus according to claim 17, wherein the cut-off value of the membrane of the main treatment unit is between about 20,000 Daltons and about 40,000 Daltons, and wherein the cut-off value of the membrane of the auxiliary treatment unit is between about 2,000 Daltons and about 10,000 Daltons.

\* \* \* \* \*